United States Patent
Bae et al.

(10) Patent No.: US 11,672,438 B2
(45) Date of Patent: Jun. 13, 2023

(54) HEMODYNAMICS MONITORING METHOD, SYSTEM AND NON-TRANSITORY COMPUTER-READABLE RECORDING MEDIUM

(71) Applicant: KOREA ADVANCED INSTITUTE OF SCIENCE AND TECHNOLOGY, Daejeon (KR)

(72) Inventors: Hyeon Min Bae, Daejeon (KR); Jong Kwan Choi, Daejeon (KR); Min Gyu Choi, Daejeon (KR); Gun Pil Hwang, Daejeon (KR); Min Su Ji, Daejeon (KR); Jae Myoung Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 669 days.

(21) Appl. No.: 16/324,628

(22) PCT Filed: Jul. 5, 2017

(86) PCT No.: PCT/KR2017/007152
§ 371 (c)(1),
(2) Date: Feb. 11, 2019

(87) PCT Pub. No.: WO2018/030643
PCT Pub. Date: Feb. 15, 2018

(65) Prior Publication Data
US 2019/0216341 A1    Jul. 18, 2019

(30) Foreign Application Priority Data

Aug. 10, 2016 (KR) .................. 10-2016-0101610

(51) Int. Cl.
*A61B 5/026* (2006.01)
*A61B 5/1455* (2006.01)
(Continued)

(52) U.S. Cl.
CPC .............. *A61B 5/0261* (2013.01); *A61B 5/00* (2013.01); *A61B 5/1071* (2013.01);
(Continued)

(58) Field of Classification Search
None
See application file for complete search history.

(56) References Cited

U.S. PATENT DOCUMENTS

2005/0222502 A1* 10/2005 Cooper ................ A61B 5/1495
                                                    600/323
2013/0204143 A1*  8/2013 Narusawa ........... A61B 5/7214
                                                    600/479

FOREIGN PATENT DOCUMENTS

JP    2006-102190 A    4/2006
JP    2009-101057 A    5/2009
(Continued)

OTHER PUBLICATIONS

"Using LEDs as Light-Level Sensors and Emitters," Altera White Paper 01076-2.1, Oct. 2009 (Year: 2009).*
(Continued)

*Primary Examiner* — Matthew Kremer
(74) *Attorney, Agent, or Firm* — Dinsmore & Shohl LLP; Yongsok Choi, Esq.

(57) ABSTRACT

According to one aspect of the invention, there is provided a method for monitoring hemodynamics, comprising the steps of: acquiring information on a posture of a first subject wearing a monitoring device; estimating a motion artifact predicted to be included in a spectroscopic measurement signal from the first subject which is measured by the monitoring device, with reference to the acquired information on the posture of the first subject, and a motion artifact estimation model for defining a correlation between a posture of at least one subject and a motion artifact occurring in a signal measured from the at least one subject; and remov-
(Continued)

ing the estimated motion artifact from the measurement signal from the first subject.

9 Claims, 8 Drawing Sheets

(51) Int. Cl.
*A61B 5/00* (2006.01)
*A61B 5/107* (2006.01)
*A61B 5/11* (2006.01)
*G01N 21/359* (2014.01)

(52) U.S. Cl.
CPC .......... *A61B 5/1116* (2013.01); *A61B 5/1455* (2013.01); *A61B 5/14553* (2013.01); *A61B 5/6803* (2013.01); *G01N 21/359* (2013.01)

(56) References Cited

FOREIGN PATENT DOCUMENTS

| KR | 10-2002-0064337 A | 8/2002 |
| KR | 10-1190351 B1 | 10/2012 |
| KR | 10-2016-0035212 A | 3/2016 |

OTHER PUBLICATIONS

International Search Report for PCT/KR2017/007152 dated Oct. 13, 2017.

* cited by examiner

FIB. 1B

HEMODYNAMICS MONITORING METHOD, SYSTEM AND NON-TRANSITORY COMPUTER-READABLE RECORDING MEDIUM

CROSS-REFERENCE TO RELATED APPLICATION(S)

This application is a national phase of Patent Cooperation Treaty (PCT) international application Serial No. PCT/KR2017/007152, filed on Jul. 5, 2017, which claims priority to Korean Patent Application Serial No. 10-2016-0101610, filed on Aug. 10, 2016. The entire contents of PCT international application Serial No. PCT/KR2017/007152, and Korean Patent Application Serial No. 10-2016-0101610 are hereby incorporated by reference.

FIELD OF THE INVENTION

The present invention relates to a method, system, and non-transitory computer-readable recording medium for monitoring hemodynamics.

BACKGROUND

Near-infrared spectroscopy (NIRS) is a method for indirectly analyzing the activity occurring in a body part (e.g., a brain) of a person by measuring the degree of attenuation of near-infrared light (due to scattering and absorption by oxidized or non-oxidized hemoglobin) which varies with hemodynamic changes (e.g., changes in concentrations of oxidized and non-oxidized hemoglobin) due to the activity of the body part. More specifically, when hemodynamic changes due to the neural activity occurring in a brain is monitored, for example, near-infrared light having a wavelength range of about 630 nm to 1300 nm may be transmitted through a skull of the person to the depth of about 1 cm to 3 cm from the skull. By irradiating such near-infrared light to a head part of the person and detecting near-infrared light reflected or scattered therefrom, it is possible to monitor hemodynamic changes (e.g., a change in a concentration of blood oxygen (i.e., oxidized hemoglobin)) occurring in the cerebral cortex of the person.

According to the recently introduced near-infrared spectroscopy, the neural activity occurring in a human brain (particularly, a cortex) may be quantified by arranging near-infrared light irradiation or detection modules called optodes at predetermined intervals in various parts of a head of a person, and analyzing signals related to hemodynamics (e.g., optical density (OD) signals based on the near-infrared spectroscopy) acquired from the optodes.

Meanwhile, a subject wearing a device for monitoring hemodynamic changes due to brain activity may take a posture in which his/her head is tilted or make a motion of tilting the head during measurement, and motion artifacts may accordingly occur in the signals measured in the monitoring device due to the above posture or motion of the subject. Such motion artifacts are caused by a deterioration in the state of contact between the optodes and the scalp, or a rapid change in blood volume in the cerebral blood vessels.

A conventional technique for removing such motion artifacts has been introduced which detects a posture or motion of a subject using a motion sensor such as a gyroscope sensor or acceleration sensor, and correcting a measurement signal directly on the basis of information on the detected posture or motion (e.g., a standard deviation of data on the posture or motion), thereby removing the motion artifacts.

However, according to the above conventional technique, there is a limitation in that it is difficult to consider all the various factors causing the motion artifacts in a deductive manner, and thus the accuracy of removing the motion artifacts is not high. Further, there is a problem that a lot of operation resources are required to remove the motion artifacts, and thus real-time processing thereof is difficult.

In this connection, the inventor(s) present a technique for constructing a motion artifact estimation model for defining a correlation between a posture of a subject and a motion artifact, and removing the motion artifact from a measurement signal from the subject accurately and efficiently using the motion artifact estimation model.

SUMMARY OF THE INVENTION

One object of the present invention is to solve all the above-described problems.

Another object of the invention is to provide a method, system, and non-transitory computer-readable recording medium for accurately and efficiently removing a motion artifact from a measurement signal from a subject using a motion artifact estimation model that may be inductively derived from empirical data, by acquiring information on a posture of a first subject wearing a monitoring device; estimating a motion artifact predicted to be included in a measurement signal from the first subject which is measured by the monitoring device, with reference to the acquired information on the posture of the first subject, and a motion artifact estimation model for defining a correlation between a posture of at least one subject and a motion artifact occurring in a signal measured from the at least one subject; and removing the estimated motion artifact from the measurement signal from the first subject.

The representative configurations of the invention to achieve the above objects are described below.

According to one aspect of the invention, there is provided a method for monitoring hemodynamics, comprising the steps of: acquiring information on a posture of a first subject wearing a monitoring device; estimating a motion artifact predicted to be included in a spectroscopic measurement signal from the first subject which is measured by the monitoring device, with reference to the acquired information on the posture of the first subject, and a motion artifact estimation model for defining a correlation between a posture of at least one subject and a motion artifact occurring in a signal measured from the at least one subject; and removing the estimated motion artifact from the measurement signal from the first subject.

According to another aspect of the invention, there is provided a system for monitoring hemodynamics, comprising: a posture information management unit configured to acquire information on a posture of a first subject wearing a monitoring device; and a motion artifact removal unit configured to estimate a motion artifact predicted to be included in a spectroscopic measurement signal from the first subject which is measured by the monitoring device, with reference to the acquired information on the posture of the first subject, and a motion artifact estimation model for defining a correlation between a posture of at least one subject and a motion artifact occurring in a signal measured from the at least one subject, and to remove the estimated motion artifact from the measurement signal from the first subject.

In addition, there are further provided other methods and systems to implement the invention, as well as non-transitory computer-readable recording media having stored thereon computer programs for executing the methods.

According to the invention, it is possible to accurately and efficiently remove a motion artifact from a measurement signal from a subject using a motion artifact estimation model that may be inductively derived from empirical data.

According to the invention, it is possible to remove a motion artifact on the basis of a motion artifact estimation model that may be constructed in advance before hemodynamics monitoring proceeds, thereby enabling post-processing and real-time processing of a measurement signal.

BRIEF DESCRIPTION OF THE DRAWINGS

FIG. 1B schematically shows the external configuration of a monitoring system according to one embodiment of the invention.

DETAILED DESCRIPTION

Figure 1A:
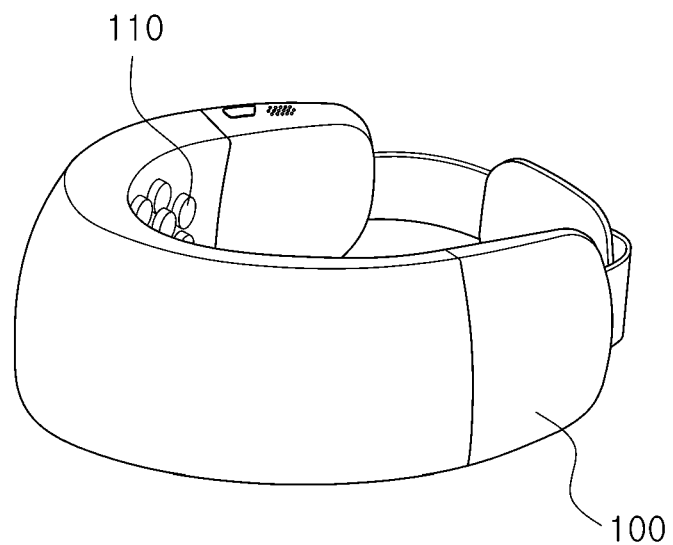
FIG. 1A schematically shows the external configuration of a monitoring system according to one embodiment of the invention.
Figure 1A:
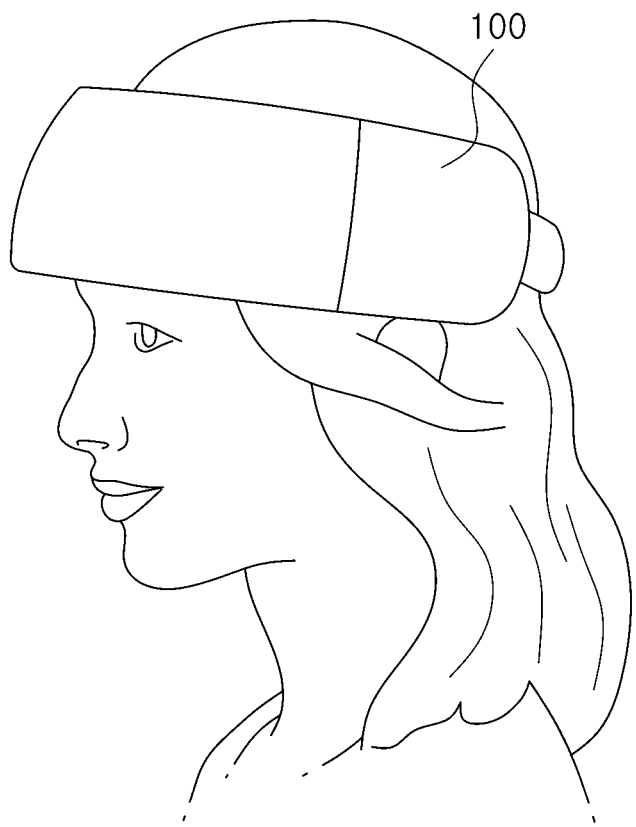

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the positions or arrangements of individual elements within each of the disclosed embodiments may also be modified without departing from the spirit and scope of the invention. Therefore, the following detailed description is not to be taken in a limiting sense, and the scope of the invention, if properly described, is limited only by the appended claims together with all equivalents thereof. In the drawings, like reference numerals refer to the same or similar functions throughout the several views.

Hereinafter, preferred embodiments of the present invention will be described in detail with reference to the accompanying drawings to enable those skilled in the art to easily implement the invention.

Herein, hemodynamics to be monitored by the monitoring device and the monitoring system may include blood composition (e.g., oxyhemoglobin concentration, deoxyhemoglobin concentration, blood oxygen saturation, etc.), blood flow, and blood volume.

Configuration of the Monitoring System

Hereinafter, the internal configuration of a monitoring system 200 and a monitoring device 100 crucial for implementing the invention and the functions of the respective components thereof will be discussed.

FIGS. 1A and 1B schematically show the external configuration of the monitoring device according to one embodiment of the invention.

Referring to FIGS. 1A and 1B, the monitoring device 100 according to one embodiment of the invention may be worn on a body part (e.g., a head part) of a subject (see FIG. 1B), and may function to measure a signal from the subject and process or analyze the measured signal as will be described below, thereby monitoring the activity occurring in the body part of the subject (e.g., the neural activity occurring in the brain).

Specifically, the monitoring device 100 according to one embodiment of the invention may include a plurality of optodes 110 for irradiating near-infrared light to a head part of a subject and detecting near-infrared light reflected or scattered from the head part of the subject (more specifically, from the cerebral venous blood of the subject) (see FIG. 1A).

For example, optical density (OD) signals based on near-infrared spectroscopy may be measured by the plurality of optodes 110 included in the monitoring device 100 according to one embodiment of the invention.

Figure 2:
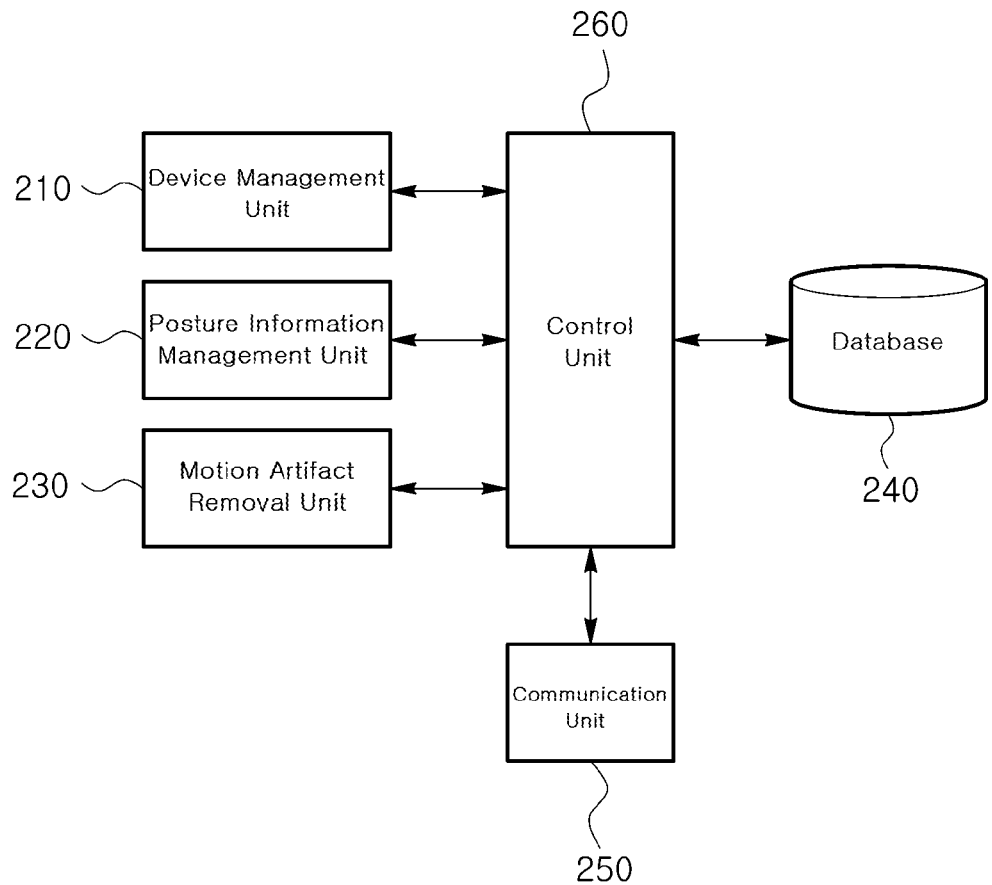
FIG. 2 illustratively shows the internal configuration of a monitoring system according to one embodiment of the invention.

FIG. 2 illustratively shows the internal configuration of the monitoring system according to one embodiment of the invention.

Referring to FIG. 2, the monitoring system 200 according to one embodiment of the invention may comprise a device management unit 210, a posture information management unit 220, a motion artifact removal unit 230, a database 240, a communication unit 250, and a control unit 260. According to one embodiment of the invention, at least some of the device management unit 210, the posture information management unit 220, the motion artifact removal unit 230, the database 240, the communication unit 250, and the control unit 260 may be program modules to communicate with an external system (not shown). The program modules may be included in the monitoring system 200 in the form of operating systems, application program modules, and other program modules, while they may be physically stored in a variety of commonly known storage devices. Further, the program modules may also be stored in a remote storage device that may communicate with the monitoring system 200. Meanwhile, such program modules may include, but not limited to, routines, subroutines, programs, objects, components, data structures, and the like for performing specific tasks or executing specific abstract data types as will be described below in accordance with the invention.

Meanwhile, although the monitoring system 200 has been described as above, the above description is illustrative, and it will be apparent to those skilled in the art that at least a part of the components or functions of the monitoring system 200 may be implemented or included in the monitoring device 100 (which is a portable device worn on a body part of a subject), as necessary. Further, in some cases, all of the functions and components of the monitoring system 200 may be implemented or included in the monitoring device 100.

First, according to one embodiment of the invention, the device management unit 210 may function to manage the monitoring device 100 such that the plurality of optodes 110 included in the monitoring device 100 may irradiate near-infrared light to a body part (e.g., a head part) of a subject and detect near-infrared light reflected or scattered from the body part of the subject. Further, the device management unit 210 according to one embodiment of the invention may manage other functions or components of the monitoring device 100 which are required to monitor hemodynamics of the subject.

Next, according to one embodiment of the invention, the posture information management unit 220 may function to acquire information on a posture of a subject wearing the monitoring device 100. Specifically, the posture information management unit 220 according to one embodiment of the invention may acquire information on a direction and angle of tilt of a body part (e.g., a head part) where the monitoring device 100 is worn.

To this end, the monitoring device 100 according to one embodiment of the invention may include at least one technical means for acquiring physical information on a posture or motion of the monitoring device 100 worn on a body part (e.g., a head part) of a subject. Examples of the technical means may include commonly known components like sensing modules such as a motion sensor, an acceleration sensor, a gyroscope, a magnetic sensor, a positioning module (e.g., a GPS module, a beacon-based positioning (position identification) module, etc.), a barometer, a distance sensor, and a camera. Further, the monitoring device 100 according to one embodiment of the invention may include a technical means for acquiring physical information on a posture or motion of a specific body part of a subject wearing the monitoring device 100 on the basis of biometric information acquired from the body of the subject. Examples of the technical means may include sensing modules such as an electromyogram signal measurement apparatus.

Figure 3:
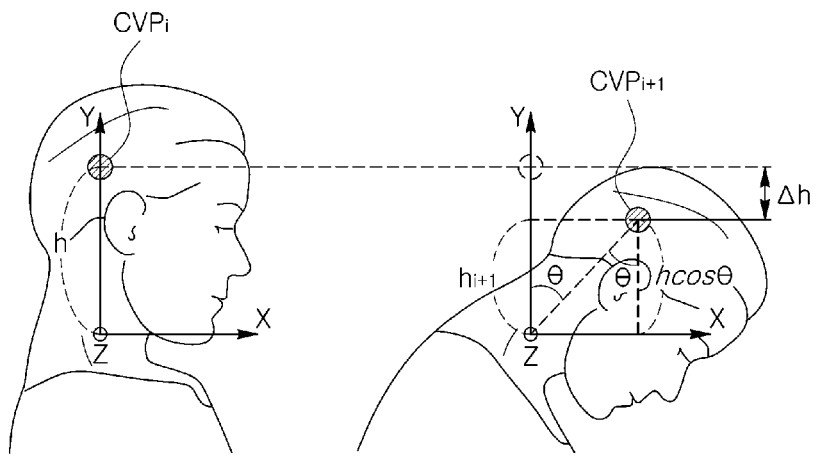
FIG. 3 illustratively shows postures that a subject may take according to one embodiment of the invention.

FIG. 3 illustratively shows postures that a subject may take according to one embodiment of the invention.

Referring to FIG. 3, it may be assumed that a subject wearing the monitoring device 100 on his/her head takes a posture of tilting the head forward by $\theta$ (i.e., rotating the head by $\theta$ in the positive (+) direction about the Z-axis in FIG. 3). In this case, pressure $CVP_{i+1}$ applied to cerebral venous blood of the subject while the subject takes the posture of tilting the head may be higher than pressure $CVP_i$ applied to the cerebral venous blood of the subject while the subject takes an upright posture without tilting the head, and a pressure increase $\Delta CVP$ may be proportional to a factor $(1-\cos \theta)$ that represents the difference in the height of the head of the subject as a ratio.

Referring further to FIG. 3, when the pressure applied to the cerebral venous blood is increased as the subject takes the posture of tilting the head, the amount of blood flowing through the cerebral veins may also be increased, and accordingly the degree in which near-infrared light irradiated to the head part of the subject for monitoring of the invention is absorbed by the cerebral venous blood may be increased. Consequently, the intensity of a measurement signal from the subject which is measured by the monitoring device 100 (more specifically, an optical density signal based on near-infrared spectroscopy) may also be increased. Hereinafter, a method for removing a motion artifact due to the posture of the subject from the measurement signal from the subject using the above correlation will be described in detail.

Next, according to one embodiment of the invention, the motion artifact removal unit 230 may function to estimate a motion artifact predicted to be included in a spectroscopic measurement signal from a first subject (who is currently being monitored) measured by the monitoring device 100, with reference to information on a posture of the first subject, and a motion artifact estimation model for defining a correlation between a posture of at least one subject and a motion artifact occurring in a signal measured from the at least one subject. Specifically, according to one embodiment of the invention, the estimated motion artifact may be specified by an intensity variation and time delay occurring in the measurement signal from the first subject measured by the monitoring device 100.

Further, according to one embodiment of the invention, the motion artifact removal unit 230 may function to remove the estimated motion artifact from the measurement signal from the first subject which is actually measured by the monitoring device 100. Specifically, according to one embodiment of the invention, the motion artifact removal unit 230 may perform real-time processing for removing the motion artifact in real time from the measurement signal from the first subject which is being measured by the monitoring device 100, as well as post-processing for removing the motion artifact from the measurement signal from the first subject after the measurement signal has been all measured by the monitoring device 100.

Here, according to one embodiment of the invention, the signal from the subject measured by the monitoring device 100 may be an optical density signal representing the amount of blood flowing through the cerebral veins on the basis of near-infrared spectroscopy. Further, according to one embodiment of the invention, the motion artifact predicted to be included in the signal from the subject measured by the monitoring device 100 may be specified by an intensity variation and time delay of the optical density signal.

Meanwhile, according to one embodiment of the invention, the motion artifact removal unit 230 may derive (or construct) a motion artifact estimation model in advance, by using empirical data on a posture of at least one subject and a motion artifact occurring in a signal measured from the at least one subject.

Specifically, when the at least one subject (who may include the above first subject) takes postures of tilting his/her head by various angles in various directions (e.g., forward, backward, leftward, rightward, etc.) while wearing the monitoring device 100 on the head, the motion artifact removal unit 230 according to one embodiment of the invention may collect information on each of the various postures taken by the at least one subject, and information on an intensity variation and time delay occurring in an optical density signal from the at least one subject measured by the monitoring device 100 when the at least one subject takes each of the various postures. Further, on the basis of the collected information, the motion artifact removal unit 230 according to one embodiment of the invention may derive a correlation between a posture taken by the subject and an intensity variation and time delay occurring in the optical density signal from the subject in correspondence to the posture, thereby constructing a motion artifact estimation model.

For example, the correlation between an angle $\theta$ by which the head of the subject is titled in a specific direction with respect to the direction of gravity and an intensity variation $\Delta OD$ of the optical density signal occurring in correspondence to the angle may be defined as a product of a factor $(1-\cos \theta)$ that indirectly represents the degree of variation in the pressure applied to the cerebral venous blood, and a gain $G$ that is derived as a relative ratio between an intensity of a virtual optical density signal to which the above factor is reflected and an intensity of an actually measured optical density signal (i.e., $\Delta OD = G (1-\cos \theta)$).

Further, for example, the correlation between an angle $\theta$ by which the head of the subject is titled with respect to the direction of gravity and a time delay of the optical density signal occurring in correspondence to the angle may be defined as an interval between a point of time when the subject takes a posture of tilting the head by $\theta$ in a specific direction with respect to the direction of gravity, and a point of time when a significant intensity variation occurs in an actually measured optical density signal.

Furthermore, the motion artifact removal unit 230 according to one embodiment of the invention may derive a motion artifact estimation model for each wavelength band of near-infrared light irradiated to the head part (or cerebral cortex part) of the subject by the monitoring device 100 or detected from the head part (or cerebral cortex part) of the subject. Further, the motion artifact removal unit 230 according to one embodiment of the invention may derive a motion artifact estimation model for each of a plurality of channels corresponding to the plurality of optodes included in the monitoring device 100.

For example, in a channel corresponding to an optode arranged at the frontal or occipital lobe part of the subject, there may be a correlation where an optical density signal from the subject varies in correspondence to the head of the subject being tilted forward or backward with respect to the direction of gravity (i.e., being rotated about the Z-axis in FIG. 3). As another example, in a channel corresponding to an optode arranged at the left or right temporal lobe part of the subject, there may be a correlation where an optical density signal from the subject varies in correspondence to the head of the subject being tilted leftward or rightward with respect to the direction of gravity (i.e., being rotated about the X-axis in FIG. 3).

Figure 4A:
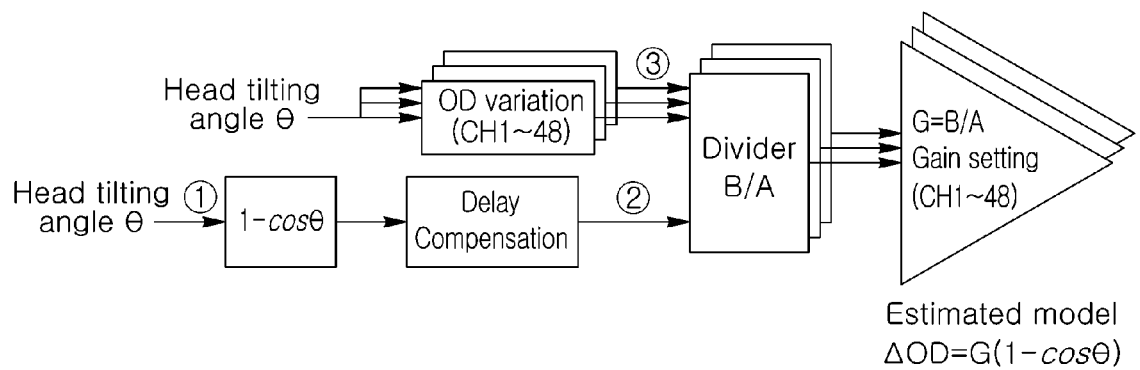
FIG. 4A illustratively shows how a motion artifact estimation model is derived on the basis of a correlation between a direction and angle of tilt of a user's head and a variation of an optical density signal occurring in correspondence to the angle according to one embodiment of the invention.
Figure 4B:
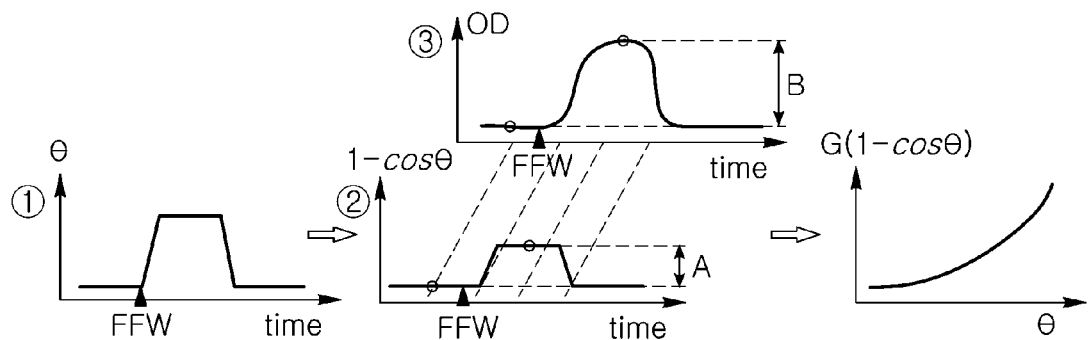
FIG. 4B illustratively shows how a motion artifact estimation model is derived on the basis of a correlation between a direction and angle of tilt of a user's head and a variation of an optical density signal occurring in correspondence to the angle according to one embodiment of the invention.

FIGS. 4A and 4B illustratively show how a motion artifact estimation model is derived on the basis of a correlation between a direction and angle of tilt of a user's head and a variation of an optical density signal occurring in correspondence to the angle according to one embodiment of the invention.

Referring to FIGS. 4A and 4B, it may be assumed that a motion artifact estimation model is derived for each of 48 channels (i.e., CH1 to CH48 in FIG. 4A) corresponding to 48 optodes included in the monitoring device 100. In this case, the motion artifact removal unit 230 according to one embodiment of the invention may compare an intensity (A in FIGS. 4A and 4B) of a virtual optical density signal (i.e., a signal corresponding to ② in FIGS. 4A and 4B) which represents, as a ratio, the degree in which pressure applied to cerebral venous blood varies as a head of at least one subject is tilted by $\theta$ in a predetermined direction with respect to the direction of gravity, and an intensity (B in FIGS. 4A and 4B) of an optical density signal from the at least one subject (i.e., a signal corresponding to ③ in FIGS. 4A and 4B) which is actually measured by the monitoring device 100, thereby deriving a gain (G in FIGS. 4A and 4B) between the above two signals.

Referring further to FIGS. 4A and 4B, the motion artifact removal unit 230 according to one embodiment of the invention may derive a motion artifact estimation model where an intensity variation $\Delta OD$ (i.e., an intensity of a motion artifact), which may occur in the optical density signal from the subject as the head of the subject is tilted by $\theta$ in a predetermined direction with respect to the direction of gravity, is estimated to be a product of the derived gain G and a factor $(1-\cos \theta)$ that represents the degree of variation in the pressure applied to the cerebral venous blood as a relative ratio (i.e., $\Delta OD = G (1-\cos \theta)$). Meanwhile, according to one embodiment of the invention, the motion artifact estimation model may be derived for each of the plurality of channels (i.e., for each of the plurality of optodes 110 included in the monitoring device 100) as mentioned above.

Meanwhile, according to one embodiment of the invention, the motion artifact removal unit 230 may not only refer to a motion artifact estimation model stored (or constructed) in advance, but also refresh an existing motion artifact estimation model on the basis of newly acquired information (i.e., information on a newly detected posture of the subject and information on a newly acquired measurement signal from the subject).

Meanwhile, a subject usually has unique physical characteristics (e.g., blood vessel wall resistance, blood viscosity, etc.) that are distinguished from those of other subjects, and thus, even if each of a plurality of subjects takes a posture of tilting a head by the same angle, a time delay and a slope of variation occurring in a measurement signal due to that posture may be different for each subject.

Therefore, according to one embodiment of the invention, the motion artifact removal unit 230 may derive a motion artifact estimation model that is personalized for each subject, with reference to a time delay and a slope of variation differently occurring in a measurement signal for each subject.

FIGS. 5 to 7B illustratively show how a personalized motion artifact estimation model is derived according to one embodiment of the invention.

In the embodiment of FIGS. 5 to 7B, a time delay occurring in a measurement signal (i.e., an optical density (OD) signal) may be specified as an interval $T_{delay}$ between a point of time when a variation starts to occur in an angle θ by which a head of a subject is tilted in a specific direction with respect to the direction of gravity (e.g., when 1% of a total amount of variation is reached), and a point of time when a variation starts to occur in the measurement signal (OD) from the subject (e.g., when 1% of a total amount of variation is reached).

Further, in the embodiment of FIGS. 5 to 7B, a slope of variation occurring in a measurement signal (i.e., an optical density (OD) signal) may be specified as an interval τ between a point of time when a variation starts to occur in the measurement signal (OD) from the subject (e.g., when 1% of a total amount of variation is reached), and a point of time when a significant level of variation has occurred in the measurement signal (OD) from the subject (e.g., when 63% of a total amount of variation is reached).

Figure 5:
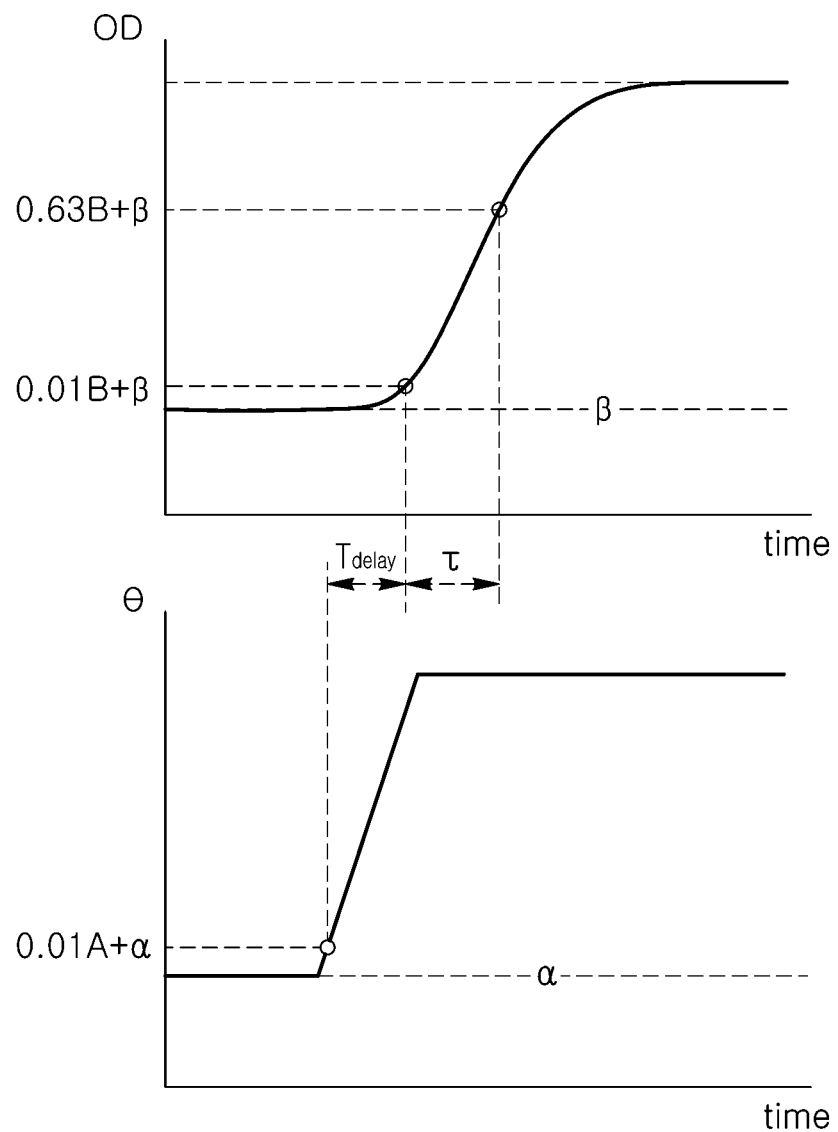
FIG. 5 illustratively shows how a personalized motion artifact estimation model is derived according to one embodiment of the invention.

First, referring to FIG. 5, the motion artifact removal unit 230 according to one embodiment of the invention may derive a time delay $T_{delay}$ and a slope of variation τ for each subject from a posture variation θ and a measurement signal OD of each subject, and may derive a human variation compensation filter personalized for each subject on the basis of the derived time delay and slope of variation for each subject.

Figure 6:
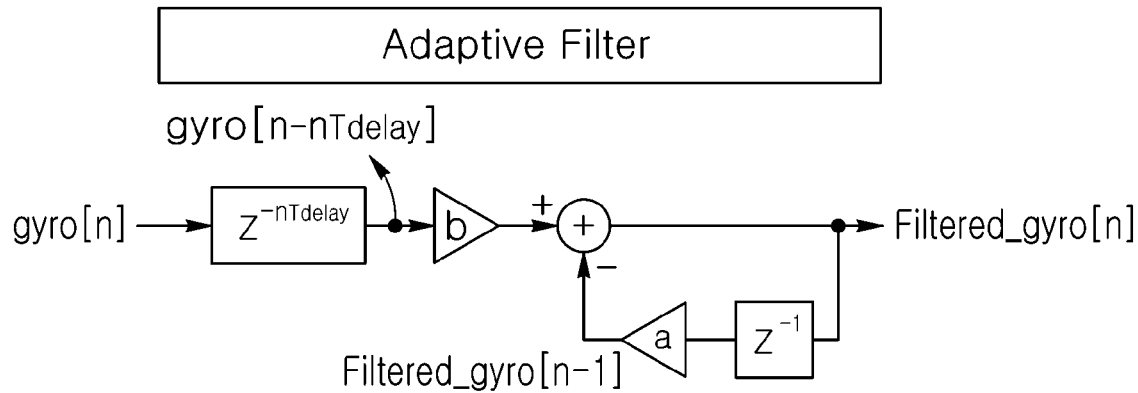
FIG. 6 illustratively shows how a personalized motion artifact estimation model is derived according to one embodiment of the invention.

Next, referring to FIG. 6, the compensation filter personalized for each subject may be defined as a primary IIR (Infinite Impulse Response) filter. According to one embodiment of the invention, in the primary IIR filter shown in FIG. 6, a time delay $nT_{delay}$ corresponding to the above time delay $T_{delay}$ may be applied, and a constant a may be determined on the basis of the derived slope of variation τ while a constant b may be determined as an arbitrary positive number.

Figure 7A:
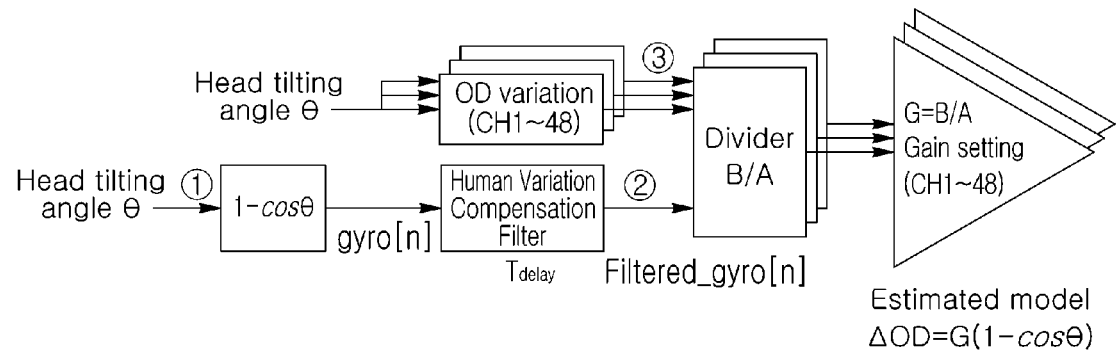
FIG. 7A illustratively shows how a personalized motion artifact estimation model is derived according to one embodiment of the invention.
Figure 7B:
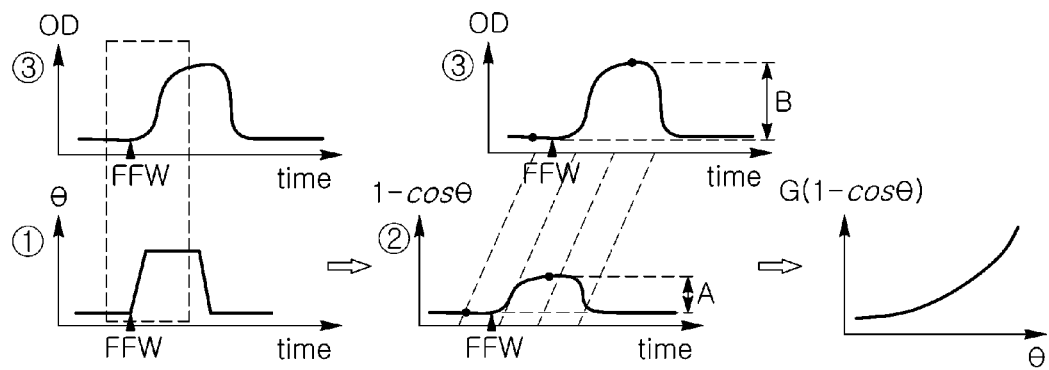
FIG. 7B illustratively shows how a personalized motion artifact estimation model is derived according to one embodiment of the invention.

Next, referring to FIGS. 7A and 7B, it may be assumed that a personalized motion artifact estimation model is derived for each of 48 channels (i.e., CH1 to CH48 in FIG. 7A) corresponding to 48 optodes included in the monitoring device 100. In this case, the motion artifact removal unit 230 according to one embodiment of the invention may compare an intensity (A in FIGS. 7A and 7B) of a virtual optical density signal filtered_gyro[n] (i.e., a signal corresponding to ② in FIGS. 7A and 7B) derived as a result of applying the human variation compensation filter personalized for each subject to a signal gyro[n] (i.e., 1−cos θ) which represents, as a ratio, the degree in which pressure applied to cerebral venous blood varies as a head of at least one subject is tilted by θ in a predetermined direction with respect to the direction of gravity, and an intensity (B in FIGS. 7A and 7B) of an optical density signal from the subject (i.e., a signal corresponding to ③ in FIGS. 7A and 7B) which is actually measured by the monitoring device 100, thereby deriving a gain (G in FIGS. 7A and 7B) between the above two signals.

Referring further to FIGS. 7A and 7B, the motion artifact removal unit 230 according to one embodiment of the invention may derive a motion artifact estimation model where an intensity variation ΔOD (i.e., an intensity of a motion artifact), which may occur in the optical density signal from the subject as the head of the subject is tilted by θ in a predetermined direction with respect to the direction of gravity, is estimated to be a product of the derived gain G and a factor (1−cos θ) that represents the degree of variation in the pressure applied to the cerebral venous blood as a relative ratio (i.e., ΔOD=G (1−cos θ)). Meanwhile, according to one embodiment of the invention, the motion artifact estimation model may be derived for each of the plurality of channels (i.e., for each of the plurality of optodes 110 included in the monitoring device 100) as mentioned above.

Figure 8A:
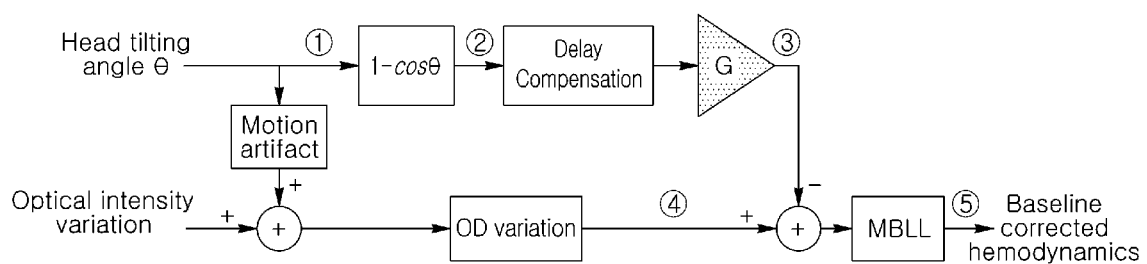
FIG. 8A illustratively shows how a motion artifact is removed from a measurement signal from a subject according to one embodiment of the invention.
Figure 8B:
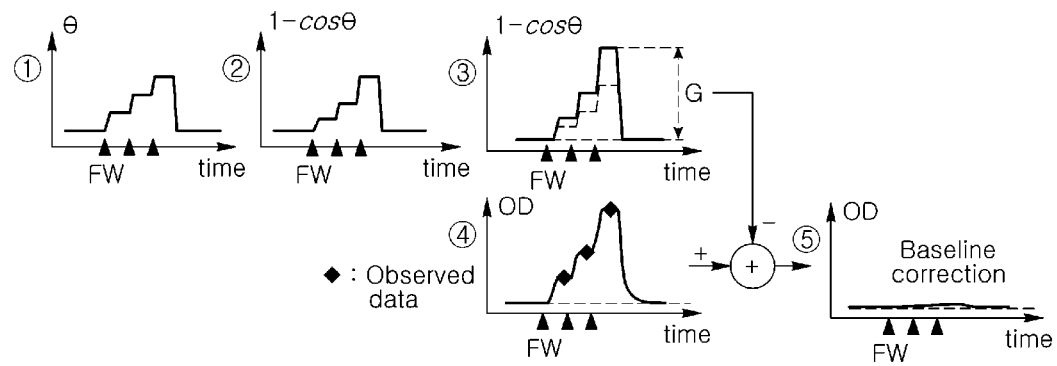
FIG. 8B illustratively shows how a motion artifact is removed from a measurement signal from a subject according to one embodiment of the invention.

FIGS. 8A and 8B illustratively show how a motion artifact is removed from a measurement signal from a subject according to one embodiment of the invention.

Referring to FIGS. 8A and 8B, it may be assumed that a motion artifact is removed from an optical density signal from a first subject which is actually measured through a specific channel corresponding to a specific optode included in the monitoring device 100. In this case, with reference to posture information indicating that a head of the first subject wearing the monitoring device 100 is tilted by θ in a specific direction with respect to the direction of gravity, and a motion artifact estimated on the basis of a motion artifact estimation model (i.e., an intensity variation and time delay that are predicted, on the basis of the motion artifact estimation model, to occur in the optical density signal from the first subject in correspondence to the head of the first subject being tilted by θ in the specific direction with respect to the direction of gravity), the motion artifact removal unit 230 according to one embodiment of the invention may subtract the estimated motion artifact signal (i.e., a signal whose intensity is ΔOD=G (1−cos θ)) (i.e., a signal corresponding to ③ in FIGS. 8A and 8B) from the optical density signal from the first subject which is actually measured by the monitoring device 100 (i.e., a signal corresponding to ④ in FIGS. 8A and 8B), thereby deriving the optical density signal from the first subject from which the motion artifact is removed (i.e., a signal corresponding to ⑤ in FIGS. 8A and 8B).

Further, according to one embodiment of the invention, the estimated motion artifact signal may correspond to a signal resulting from a product of the gain in FIG. 7 and a virtual optical density signal, wherein the virtual optical density signal is derived by applying the human variation compensation filter personalized for each subject in FIGS. 5 to 7B to a signal (1−cos θ) that represents, as a ratio, the degree in which pressure applied to cerebral venous blood varies as a head of a subject is tilted by θ in a predetermined direction with respect to the direction of gravity.

FIGS. 9A to 10C illustratively show a result of conducting a test in which a motion artifact is removed from a measurement signal from a subject according to one embodiment of the invention.

In the embodiment of FIGS. 9A to 10C, a time delay occurring in a measurement signal from a subject A of the test (i.e., an interval between a point of time when a variation starts to occur in an angle θ by which a head of the subject A is tilted in a specific direction with respect to the direction of gravity, and a point of time when a variation starts to occur in the measurement signal from the subject A) was derived as 0.62 s, and a slope of variation occurring in the measurement signal (i.e., an interval between a point of time when a variation starts to occur in the measurement signal from the subject A, and a point of time when a significant level of variation has occurred in the measurement signal from the subject A) was derived as 2.33 s.

Figure 9A:
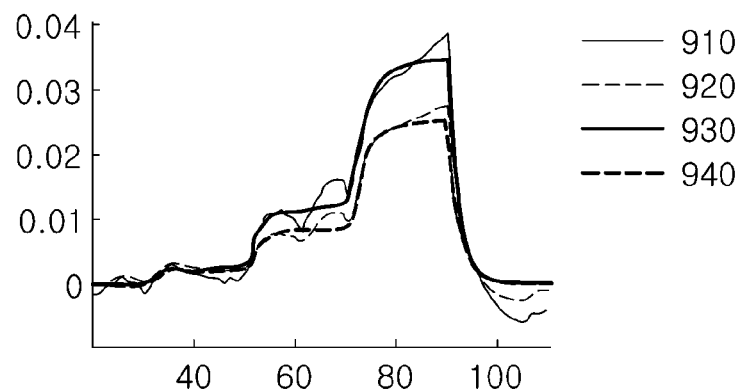
FIG. 9A illustratively shows a result of conducting a test in which a motion artifact is removed from a measurement signal from a subject according to one embodiment of the invention.
Figure 9B:
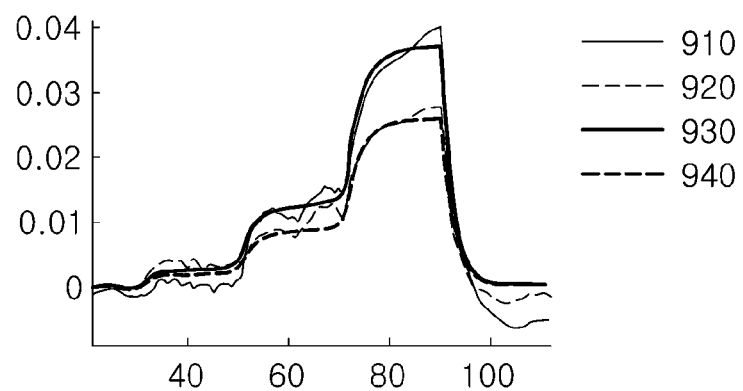
FIG. 9B illustratively shows a result of conducting a test in which a motion artifact is removed from a measurement signal from a subject according to one embodiment of the invention.
Figure 9C:
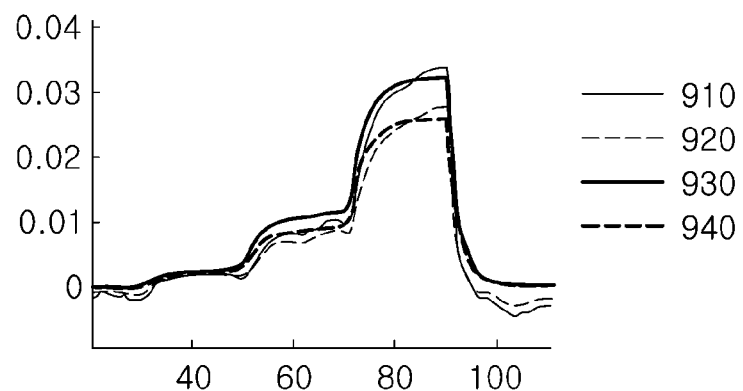
FIG. 9C illustratively shows a result of conducting a test in which a motion artifact is removed from a measurement signal from a subject according to one embodiment of the invention.

In the graphs of FIGS. 9A to 9C, a solid line 910 represents an optical density signal of a first wavelength; a dotted line 920 represents an optical density signal of a second wavelength; a bold solid line 930 represents a motion artifact signal estimated to be included in the optical density signal of the first wavelength; and a bold dotted line 940 represents a motion artifact signal estimated to be included in the optical density signal of the second wavelength. Further, in the graphs of FIGS. 10A to 10C, a solid line 1050 represents the optical density signal of the first wavelength from which the motion artifact is removed, and a dotted line 1060 represents the optical density signal of the second wavelength from which the motion artifact is removed.

Referring to FIGS. 9A to 9C, it can be seen that a measurement signal measured through each of three channels (corresponding to FIGS. 9A, 9B and 9C) provided in the monitoring device 100 worn by the subject A includes a motion artifact that greatly varies according to posture variations of the subject A.

Figure 10A:
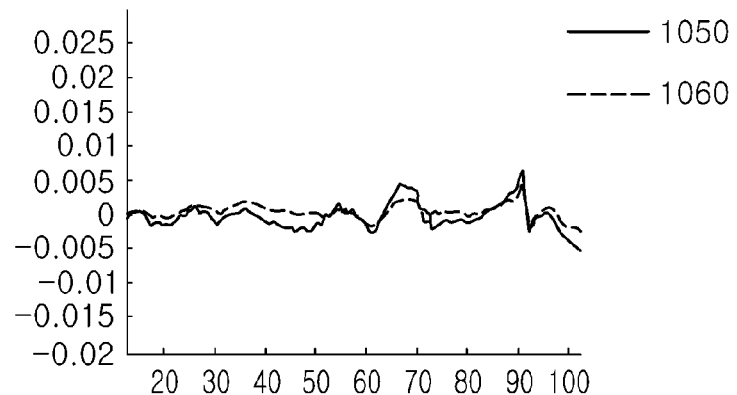
FIG. 10A illustratively shows a result of conducting a test in which a motion artifact is removed from a measurement signal from a subject according to one embodiment of the invention.
Figure 10B:
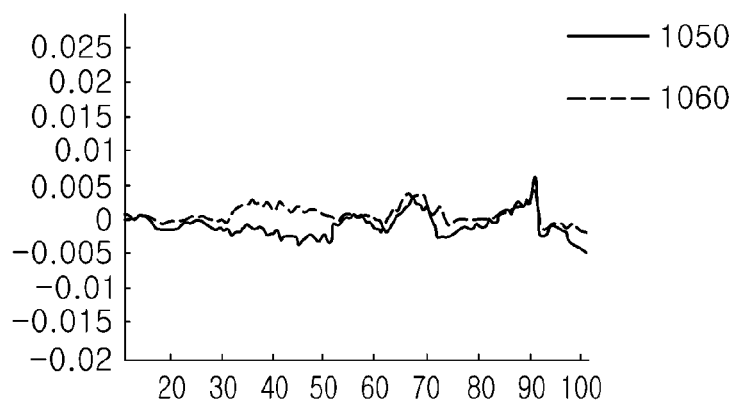
FIG. 10B illustratively shows a result of conducting a test in which a motion artifact is removed from a measurement signal from a subject according to one embodiment of the invention.
Figure 10C:
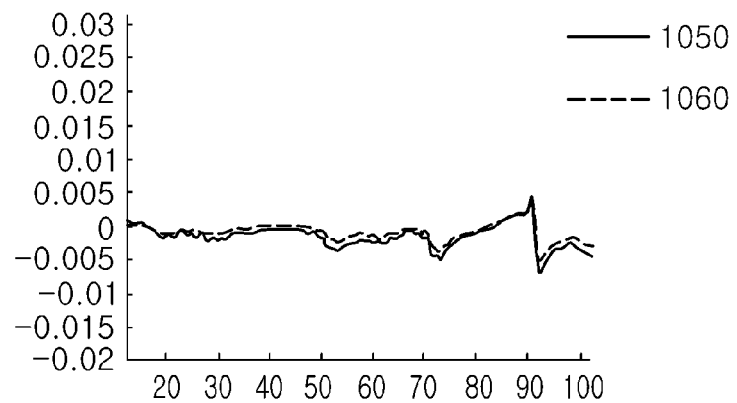
FIG. 10C illustratively shows a result of conducting a test in which a motion artifact is removed from a measurement signal from a subject according to one embodiment of the invention.

Referring to FIGS. 10A to 10C, it can be seen that for each of three channels (corresponding to FIGS. 10A, 10B and 10C) provided in the monitoring device 100, there are significantly less variations or ripples occurring in a signal 1050 or 1060 (i.e., a corrected measurement signal) derived as a result of removing the motion artifact estimated according to the invention (i.e., the bold solid line 930 or the bold dotted line 940 in FIGS. 9A to 9C) from the measurement signal from the subject A (i.e., the solid line 910 or the dotted line 920 in FIGS. 9A to 9C).

However, it is noted that the detailed configurations related to the motion artifact estimation model according to the invention are not necessarily limited to the above-described embodiments, and may be changed without limitation as long as the objects of the invention may be achieved.

Meanwhile, according to one embodiment of the invention, the database 240 may store information on a motion artifact estimation model (i.e., information on various postures that may be taken by subjects, measurement signals from the subjects corresponding to the various postures of the subjects, and correlations between the postures of the subjects and motion artifacts occurring in the measurement signals from the subjects). Further, according to one embodiment of the invention, the database 240 may also store a variety of information on monitoring performed on the basis of measurement signals from which motion artifacts are removed according to the invention. Although FIG. 2 shows that the database 240 is incorporated in the monitoring system 200, the database 240 may be configured separately from the monitoring system 200 as needed by those skilled in the art to implement the invention. Meanwhile, the database 240 according to the invention encompasses a computer-readable recording medium, and may refer not only to a database in a narrow sense but also to a database in a broad sense including file system-based data records and the like. The database 240 according to the invention may be even a collection of simple logs if one can search and retrieve data from the collection.

Meanwhile, the communication unit 250 according to one embodiment of the invention may function to enable the monitoring system 200 to communicate with an external device.

Lastly, the control unit 260 according to one embodiment of the invention may function to control data flow among the device management unit 210, the posture information management unit 220, the motion artifact removal unit 230, the database 240, and the communication unit 250. That is, the control unit 260 may control inbound data flow or data flow among the respective components of the monitoring system 200, such that the device management unit 210, the posture information management unit 220, the motion artifact removal unit 230, the database 240, and the communication unit 250 may carry out their particular functions, respectively.

Although the cases where a measurement signal from which a motion artifact is to be removed is an optical density signal based on near-infrared spectroscopy have been mainly described above, the measurement signal is not necessarily limited thereto, and it is noted that any other type of measurement signal may be assumed as long as the objects or effects of the methods, systems, and non-transitory computer-readable recording media described herein may be achieved.

Further, although the cases where a body part to be monitored is a head part (i.e., a brain) have been mainly described above, the body part to be monitored according to the invention is not necessarily limited thereto, and it is noted that any other body part that can be monitored on the basis of hemodynamics may be assumed to be the body part to be monitored according to the invention.

The embodiments according to the invention as described above may be implemented in the form of program instructions that can be executed by various computer components, and may be stored on a non-transitory computer-readable recording medium. The non-transitory computer-readable recording medium may include program instructions, data files, data structures and the like, separately or in combination. The program instructions stored on the non-transitory computer-readable recording medium may be specially designed and configured for the present invention, or may also be known and available to those skilled in the computer software field. Examples of the non-transitory computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be configured to operate as one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method for monitoring hemodynamics, comprising the steps of:
   acquiring information on a posture of a subject wearing a monitoring device;
   estimating a motion artifact predicted to be included in a measurement signal from the subject which is measured by the monitoring device, with reference to the acquired information on the posture of the subject, and a motion artifact estimation model for defining a correlation between the posture of the subject and a motion artifact occurring in the measurement signal from the subject; and
   removing the estimated motion artifact from the measurement signal from the subject,
   wherein the information on the posture of the subject is acquired from a sensing module that is included in the monitoring device and capable of acquiring the information on the posture of the subject or a motion of the monitoring device or the subject, and
   wherein the motion artifact estimation model is constructed by calculating a time delay ($T_{delay}$), which is specified as an interval between a point of time when a variation starts to occur in an angle (θ) by which the subject is tilted in a specific direction with respect to a direction of gravity and a point of time when a variation starts to occur in the measurement signal from the subject, and a duration of variation (τ), which is specified as an interval between the point of time when the variation starts to occur in the measurement signal from the subject and a point of time when a predetermined level of variation has occurred in the measurement signal from the subject;
   deriving a compensation filter personalized for the subject on a basis of the calculated time delay and the duration of variation; and
   calculating a gain (G), which is a relative ratio between an intensity of the measurement signal from the subject and an intensity of a virtual optical density signal, by comparing the measurement signal from the subject with the virtual optical density signal, the virtual optical density signal being derived from a degree of variation in pressure applied to venous blood when the subject is tilted in the specific direction with respect to the direction of gravity.

2. The method of claim 1, wherein the information on the posture of the subject includes information on a direction of a body part of the subject where the monitoring device is worn with respect to the direction of gravity, and an angle by which the body part of the subject where the monitoring device is worn is tilted with respect to the direction of gravity.

3. The method of claim 1, wherein the measurement signal from the subject is an optical density (OD) signal based on near-infrared spectroscopy (NIRS).

4. The method of claim 1, wherein the motion artifact estimation model is derived for each of a plurality of channels corresponding to a plurality of optodes included in the monitoring device.

5. The method of claim 1, wherein the motion artifact estimation model is derived for each wavelength band of near-infrared light irradiated or detected by the monitoring device.

6. A non-transitory computer-readable recording medium having stored thereon a computer program, the computer program, when executed by a processor of a monitoring device, executing:
   acquiring information on a posture of a subject wearing the monitoring device;
   estimating a motion artifact predicted to be included in a measurement signal from the subject which is measured by the monitoring device, with reference to the acquired information on the posture of the subject, and a motion artifact estimation model for defining a correlation between the posture of the subject and a motion artifact occurring in the measurement signal from the subject; and
   removing the estimated motion artifact from the measurement signal from the subject,
   wherein the information on the posture of the subject is acquired from a sensing module that is included in the monitoring device and capable of acquiring the information on the posture of the subject or a motion of the monitoring device or the subject, and
   wherein the motion artifact estimation model is constructed by calculating a time delay ($T_{delay}$), which is specified as an interval between a point of time when a variation starts to occur in an angle (θ) by which the subject is tilted in a specific direction with respect to a direction of gravity and a point of time when a variation starts to occur in the measurement signal from the subject, and a duration of variation (τ), which is specified as an interval between the point of time when the variation starts to occur in the measurement signal from the subject and a point of time when a predetermined level of variation has occurred in the measurement signal from the subject;
   deriving a compensation filter personalized for the subject on a basis of the calculated time delay and the duration of variation; and
   calculating a gain (G), which is a relative ratio between an intensity of the measurement signal from the subject and an intensity of a virtual optical density signal, by comparing the measurement signal from the subject with the virtual optical density signal, the virtual optical density signal being derived from a degree of variation in pressure applied to venous blood when the subject is tilted in the specific direction with respect to the direction of gravity.

7. A system for monitoring hemodynamics, comprising:
a monitoring device programmed to:
   acquire information on a posture of a subject wearing the monitoring device; and
   estimate a motion artifact predicted to be included in a measurement signal from the subject which is measured by the monitoring device, with reference to the acquired information on the posture of the subject, and a motion artifact estimation model for defining a correlation between the posture of the subject and a motion artifact occurring in the measurement signal from the subject; and
   remove the estimated motion artifact from the measurement signal from the subject,
   wherein a sensing module included in the monitoring device acquires the information on the posture of the subject and acquires the information on the posture of the subject or a motion of the monitoring device or the subject, and
   wherein the monitoring device is programmed to:
   calculate a time delay ($T_{delay}$), which is specified as an interval between a point of time when a variation starts to occur in an angle (θ) by which the subject is tilted in a specific direction with respect to a direction of gravity and a point of time when a variation starts to occur in the measurement signal from the subject, and a duration of variation ($\tau$), which is specified as an interval between the point of time when the variation starts to occur in the measurement signal from the subject and a point of time when a predetermined level of variation has occurred in the measurement signal from the subject;

derive a compensation filter personalized for the subject on a basis of the calculated time delay and the duration of variation; and calculate a gain (G), which is a relative ratio between an intensity of the measurement signal from the subject and an intensity of a virtual optical density signal, by comparing the measurement signal from the subject with the virtual optical density signal, the virtual optical density signal being derived from a degree of variation in pressure applied to venous blood when the subject is tilted in the specific direction with respect to the direction of gravity.

8. The system of claim 7, wherein the information on the posture of the subject includes information on a direction of a body part of the subject where the monitoring device is worn with respect to the direction of gravity, and an angle by which the body part of the subject where the monitoring device is worn is tilted with respect to the direction of gravity.

9. The system of claim 7, wherein the measurement signal from the subject is an optical density (OD) signal based on near-infrared spectroscopy (NIRS).

\* \* \* \* \*